United States Patent
Vignon et al.

(10) Patent No.: US 12,186,127 B2
(45) Date of Patent: *Jan. 7, 2025

(54) INTERLEAVED IMAGING AND TRACKING SEQUENCES FOR ULTRASOUND-BASED INSTRUMENT TRACKING

(71) Applicant: KONINKLIJKE PHILIPS N.V., Eindhoven (NL)

(72) Inventors: Francois Guy Gerard Marie Vignon, Andover, MA (US); Ramon Quido Erkamp, Swampscott, MA (US); Kunal Vaidya, Boston, MA (US); Shyam Bharat, Arlington, MA (US); Jain Ameet, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,456

(22) Filed: Mar. 26, 2023

(65) Prior Publication Data
US 2023/0225701 A1     Jul. 20, 2023

Related U.S. Application Data

(63) Continuation of application No. 16/623,023, filed as application No. PCT/EP2018/066092 on Jun. 18, 2018, now Pat. No. 11,642,097.
(Continued)

(51) Int. Cl.
A61B 34/20     (2016.01)
A61B 8/08      (2006.01)
A61B 90/00     (2016.01)

(52) U.S. Cl.
CPC ............ *A61B 8/0841* (2013.01); *A61B 34/20* (2016.02); *A61B 90/06* (2016.02); *A61B 2034/2063* (2016.02); *A61B 2090/062* (2016.02)

(58) Field of Classification Search
CPC ....... A61B 8/0841; A61B 34/20; A61B 90/06; A61B 2034/2063; A61B 2090/062; A61B 2090/3925
See application file for complete search history.

(56) References Cited

U.S. PATENT DOCUMENTS

2005/0151649 A1    7/2005  Wright et al.
2010/0249595 A1    9/2010  Xu et al.
(Continued)

FOREIGN PATENT DOCUMENTS

WO    2004084736 A1    10/2004
WO    WO-2005117710 A2 * 12/2005 ............. A61B 34/20
(Continued)

OTHER PUBLICATIONS

PCT/EP2018/066092 ISR & WO, Sep. 21, 2018, 16 Page Document.

*Primary Examiner* — Amal Aly Farag

(57) ABSTRACT

A method for tracking an interventional medical device in a patient includes interleaving, by an imaging probe external to the patient, a pulse sequence of imaging beams and tracking beams to obtain an interleaved pulse sequence. The method also includes transmitting, from the imaging probe to the interventional medical device in the patient, the interleaved pulse sequence. The method further includes determining, based on a response to the tracking beams received from a sensor on the interventional medical device, a location of the sensor in the patient.

15 Claims, 11 Drawing Sheets

Related U.S. Application Data

(60) Provisional application No. 62/521,608, filed on Jun. 19, 2017.

(56) References Cited

U.S. PATENT DOCUMENTS

| | | |
|---|---|---|
| 2012/0268415 A1 | 10/2012 | Konovalov et al. |
| 2013/0041252 A1 | 2/2013 | Vignon et al. |
| 2014/0094695 A1 | 4/2014 | Kumar et al. |
| 2014/0187942 A1 | 7/2014 | Wang et al. |
| 2014/0187946 A1 | 7/2014 | Miller et al. |
| 2015/0342572 A1 | 12/2015 | Maraghoosh et al. |

FOREIGN PATENT DOCUMENTS

| | | |
|---|---|---|
| WO | 2011138698 A1 | 11/2011 |
| WO | 2012172458 A1 | 12/2012 |

* cited by examiner

Viewpoint of imaging probe and controller

Viewpoint of imaging probe and controller

Viewpoint of imaging probe and controller

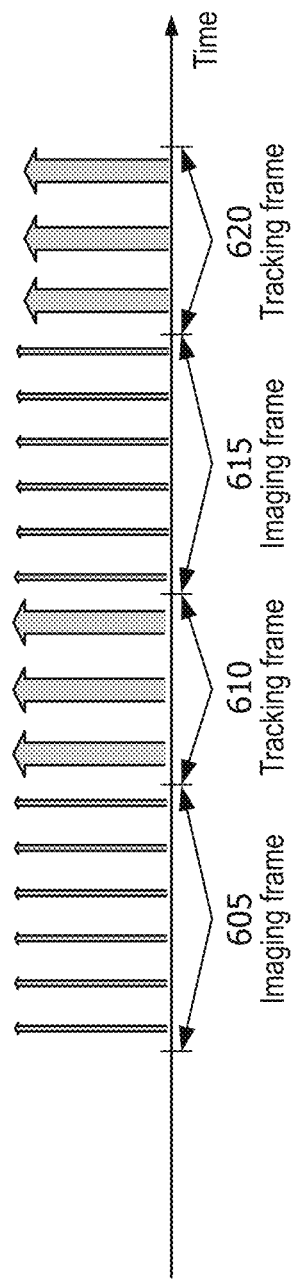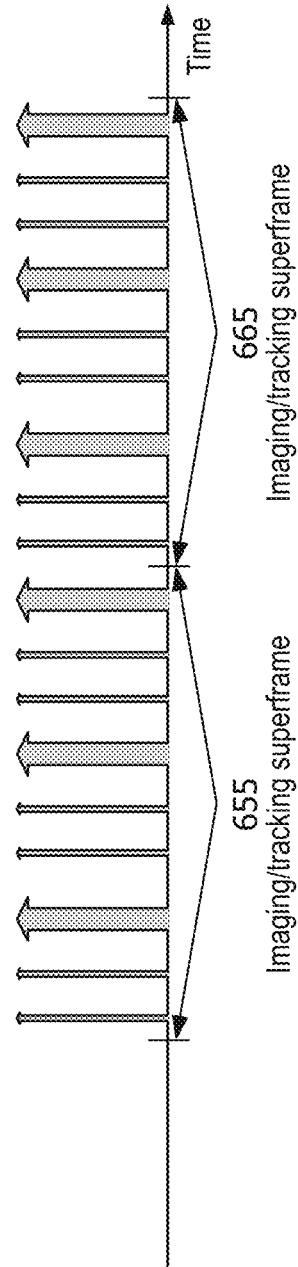

INTERLEAVED IMAGING AND TRACKING SEQUENCES FOR ULTRASOUND-BASED INSTRUMENT TRACKING

CROSS-REFERENCE TO RELATED APPLICATIONS

This application is a continuation application of U.S. patent application Ser. No. 16/623,023, filed on Dec. 16, 2019, which is a U.S. National Phase application under 35 U.S.C. § 371 of International Application No. PCT/EP2018/066092 filed Jun. 18, 2018, which claims the benefit of U.S. Patent Application No. 62/521,608, filed on Jun. 19, 2017. These applications are hereby incorporated by reference herein.

BACKGROUND

Conventionally, an ultrasound system is used to emit ultrasonic waves as imaging beams from an imaging probe. Echoes of the imaging beams are received and used to create an ultrasound image on a display. Invasive medical procedures may be made less invasive by tracking location of interventional medical devices in a patient, and a modified conventional ultrasound system can be used to perform such location tracking using only conventional ultrasound imaging beams (i.e., otherwise used for performing ultrasound imaging). An ultrasound sensor can be placed on the interventional medical device and located using ultrasound imaging beams exclusively. As the ultrasound imaging probe sweeps the imaged medium with the ultrasound imaging beams, a position of the ultrasound sensor can be estimated.

Tracking using ultrasound imaging beams exclusively may not be optimal. For example, ultrasound scanning frequencies for ultrasound imaging may be on an edge of the bandwidth of the ultrasound sensor on the interventional medical device. Also, the tracking region using ultrasound imaging beams exclusively is limited to the imaging field of view. Additional concerns include that all beamforming parameters used for ultrasound imaging beams (e.g., beam positions, repetitions, and waveform characteristics) must be provided, e.g., for use in the tracking.

SUMMARY

A method for tracking an interventional medical device in a patient includes interleaving, by an imaging probe external to the patient, a pulse sequence of imaging beams and tracking beams to obtain an interleaved pulse sequence. The method also includes transmitting, from the imaging probe to the interventional medical device in the patient, the interleaved pulse sequence. The method further includes determining, based on a response to the tracking beams received from a sensor on the interventional medical device, a location of the sensor in the patient.

A system for tracking an interventional medical device in a patient includes an imaging probe external to the patient that interleaves a pulse sequence of imaging beams and tracking beams to obtain an interleaved pulse sequence, and that transmits the interleaved pulse sequence to the interventional medical device in the patient. The system also includes a sensor on the interventional medical device that responds with a response to the tracking beams from the imaging probe. The system determines, based on the response to the tracking beams, a location of the sensor in the patient.

BRIEF DESCRIPTION OF THE DRAWINGS

The example embodiments are best understood from the following detailed descriptions of representative embodiments presented below when considered in conjunction with the accompanying figures. It is emphasized that the various features are not necessarily drawn to scale. In fact, the dimensions may be arbitrarily increased or decreased for clarity of discussion. Wherever applicable and practical, like reference numerals refer to like elements.

FIG. 6A illustrates a timing diagram for an embodiment of interleaved imaging and tracking sequences for ultrasound-based instrument tracking, in accordance with a representative embodiment.

FIG. 6B illustrates a timing diagram for another embodiment of interleaved imaging and tracking sequences for ultrasound-based instrument tracking, in accordance with a representative embodiment.

DETAILED DESCRIPTION

Figure 1A:
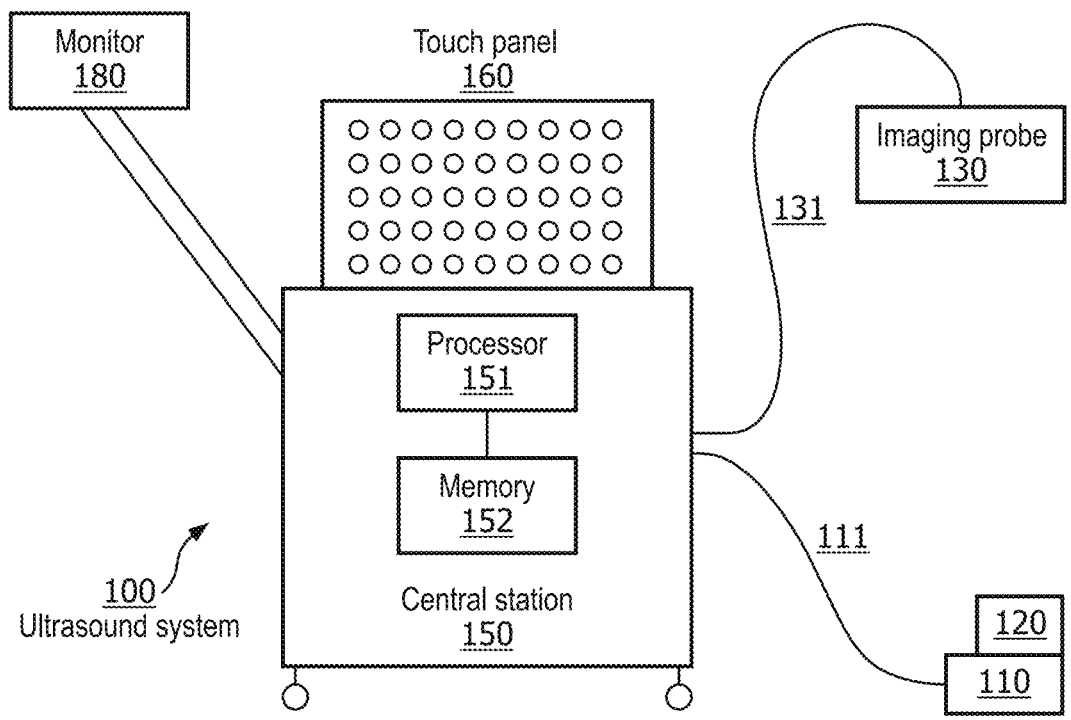
FIG. 1A illustrates an ultrasound system for interleaved imaging and tracking sequences for ultrasound-based instrument tracking, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprise", and/or "comprising," and/or similar terms when used in this specification, specify the presence of stated features, elements, and/or components, but do not preclude the presence or addition of one or more other features, elements, components, and/or groups thereof. As used herein, the term "and/or" includes all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, time-interleaved imaging frames and tracking frames (or imaging beams and tracking beams) can be tailored each to its specific purpose: imaging or tracking. The tracking beams may have characteristics (e.g., shape, position, waveforms) to optimize the tracking beams for tracking.

FIG. 1A illustrates an ultrasound system for interleaved imaging and tracking sequences for ultrasound-based instrument tracking, in accordance with a representative embodiment. In FIG. 1, an ultrasound system 100 includes a central station 150 with a processor 151 and memory 152, a touch panel 160, a monitor 180, an imaging probe 130 connected to the central station 150 by wire 131, and an interventional medical device 110 connected to the central station by wire 111. A sensor 120 is on the interventional medical device 110.

By way of explanation, an interventional medical device 110 is placed internally into a patient during a medical procedure. Locations of the interventional medical device 110 can be tracked using the sensor 120. For example, the sensor 120 may receive and use tracking beams to help determine a location of the sensor 120, in addition to the recent conventional ability to use ultrasound imaging beams to help determine the location of the sensor 120. The sensor 120 may be used passively or actively to respond to the received ultrasound tracking beams. As described herein, interleaving imaging and tracking sequences is used to selectively, typically, or always provide different imaging and tracking beams in an interleaved sequence. However, as also noted herein, the tracking can be performed using either or both of the imaging beams and tracking beams.

In FIG. 1A, wire 111 and wire 131 are used to connect the interventional medical device 110 and imaging probe 130 to the central station 150. For the imaging probe 130, a wire 131 may not present much of a concern, though the wire 131 may still be a distraction. For the interventional medical device 110, a wire 111 may be used to send back, for example, images when the interventional medical device 110 is used to capture images. However, a wire 111 may be of more concern in that the interventional medical device 110 is at least partly inserted in the patient. Accordingly, replacing the wire 131 and the wire 111 with wireless connections will provide some benefit.

Figure 1B:
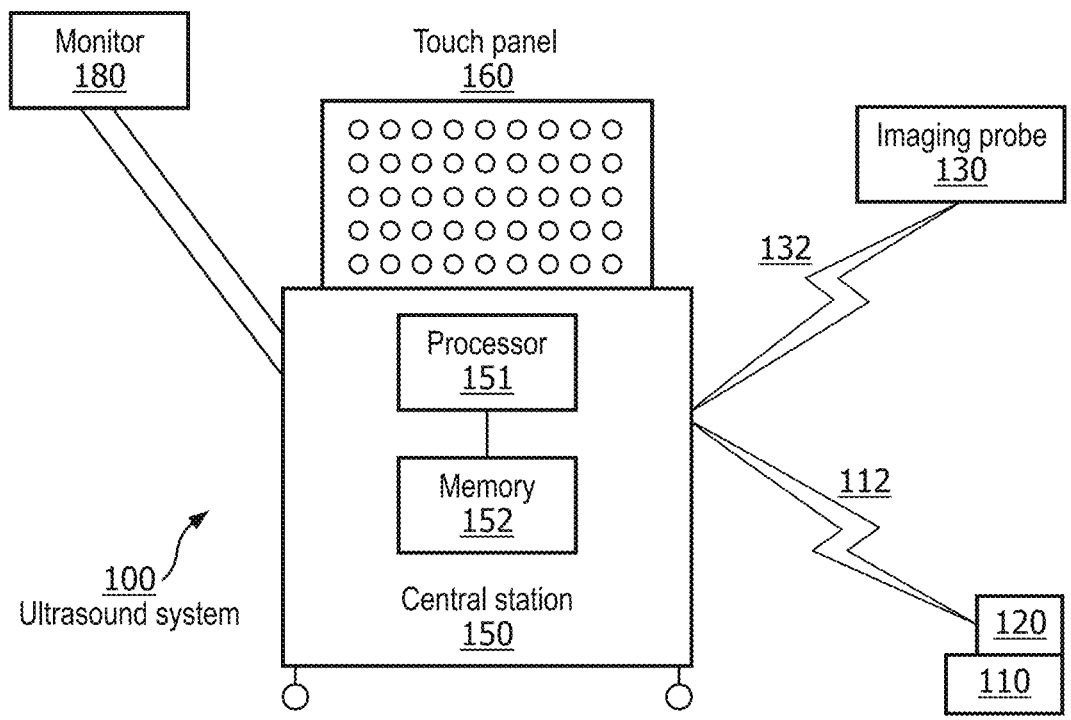
FIG. 1B illustrates another ultrasound system for interleaved imaging and tracking sequences for ultrasound-based instrument tracking, in accordance with a representative embodiment.

FIG. 1B illustrates another ultrasound system for interleaved imaging and tracking sequences for ultrasound-based instrument tracking, in accordance with a representative embodiment. In FIG. 1B, the wire 131 is replaced with wireless data connection 132, and the wire 111 is replaced with wireless data connection 112. Otherwise, the ultrasound system 100 in FIG. 1B includes the same central station 150 as in FIG. 1A, i.e., with the processor 151 and memory 152, touch panel 160, monitor 180, imaging probe 130, interventional medical device 110, and sensor 120.

In FIG. 1B, the ultrasound system 100 may be an arrangement with an interventional medical device 110 with the sensor 120 on board. The interventional medical device 110 may be, e.g., a needle with the sensor 120 at its tip. The sensor 120 may be configured to listen to and analyze data from tracking beams coming from the imaging probe 130. The "sending" of the tracking beams from the imaging probe 130, and the "listening" to the tracking beams by the sensor 120, are synchronized.

In FIG. 1A or FIG. 1B, the imaging probe 130 may send an interleaved pulse sequence of imaging beams and tracking beams. The pulse sequence may include both imaging beams and tracking beams. Mechanisms for interleaving are described herein below.

An explanation of the relationship between the central station 150, imaging probe 130 and the sensor 120 follows. In this regard, central station 150 in FIGS. 1A and 1B may include a beamformer (not shown) that is synchronized by a clock (not shown) to send properly delayed signals in a transmit mode to elements of an imaging array in the imaging probe 130. In a receive mode, the beamformer may properly delay and sum signals from the individual elements of the imaging array in the imaging probe 130. The interleaving described herein is performed using the imaging probe 130, and may be in accordance with beamforming performed by the beamformer of the central station 150.

In an alternative exemplary one-way relationship, the imaging probe 130 may emit tracking beams that impinge on the sensor 120 (i.e., when the sensor 120 is in the field of view of the tracking beams). The sensor 120 may receive and convert the energy of the tracking beams into signals so that the sensor 120, or even the interventional medical device 110, can determine the position of the sensor 120 relative to the imaging array of the imaging probe 130. The relative position of the sensor 120 can be computed geometrically based on the received tracking beams received by the sensor 120.

The central station 150 may be considered a control unit that controls the imaging probe 130. As described in FIGS. 1A and 1i, the central station 150 includes a processor 151 connected to a memory 152. The central station 150 may also include a clock (not shown) which provides clock signals to synchronize the imaging probe 130 with the sensor 120.

The imaging probe 130 is adapted to scan a region of interest that includes the interventional medical device 110 and the sensor 120. Of course, as is known for ultrasound imaging probes, the imaging probe 130 uses ultrasound imaging beams to provide images on a frame-by-frame basis. The imaging probe 130 can also use separate tracking beams to obtain the location of the sensor 120.

As noted, in the one-way relationship, the sensor 120 may be adapted to convert tracking beams provided by the imaging probe 130 into electrical signals, and to provide either the raw data from the sensor 120, or partially or completely processed data (e.g., calculated sensor location) from the sensor 120 to the central station 150, either directly or indirectly (e.g., via a transmitter or repeater located in a proximal end of the interventional medical device 110). These data, depending on their degree of processing, are either used by the central station 150 to determine the location of the sensor 120 and the location of the distal end of the interventional medical device 110 to which the sensor 120 is attached, or to provide the central station 150 with the location of the sensor 120 and the location of the distal end of the interventional medical device 110 to which the sensor 120 is attached.

As described herein, the position of the sensor 120 is determined by or provided to the central station 150. The position of the sensor 120 can be used by the processor 151 to overlay the position of the sensor 120 onto an image frame for display on the monitor 180, and thus the distal end of the interventional medical device 110 relative to the image frame. In another representative embodiment, instructions stored in memory 152 are executed by the processor 151 to determine a position of the sensor 120 relative to an image frame, and to overlay the position of the sensor 120, and thus the distal end of the interventional medical device 110 relative to the image frame.

Broadly, in operation, the processor 151 initiates a scan by the imaging probe 130. The scan can include interleaved imaging beams and tracking beams across a region of interest. The imaging beams are used to form an image of a frame; and the tracking beams are used to determine the location of the sensor 120. As can be appreciated, the image from imaging beams is formed from a two-way transmission sequence, with images of the region of interest being formed by the transmission and reflection of sub-beams. By contrast, in the one-way relationship, the tracking beams are incident on the sensor 120, which converts the tracking beams into electrical signals (i.e., rather than or in addition to reflecting the tracking beams). In the two-way relationship, the tracking beams are reflected by the sensor 120, so that the imaging probe 130 determines the location of the sensor 120 using the reflected tracking beams.

As noted above, data used to determine location of the sensor 120 may comprise raw data, partially processed data, or fully processed data, depending on where location is to be determined. Depending on the degree of processing, these data can be provided to the processor 151 for executing instructions stored in the memory 152 (i.e., of the central station 150) to determine the position of the sensor 120 in the coordinate system of ultrasound images from the beamformer. Alternatively, these data may include the determined position of the sensor 120 in the coordinate system which is used by the processor 151 when executing instructions stored in the memory 152 to overlay the position of the sensor 120 on the ultrasound image in the monitor 180. To this end, the beamformer of the central station 150 may process the beamformed signal for display as an image of a frame. The output from the beamformer can be provided to the processor 151. The data from the sensor 120 may be raw data, in which case the processor 151 executes instructions in the memory 152 to determine the position of the sensor 120 in the coordinate system of the image; or the data from the sensor 120 may be processed by the interventional medical device 110 to determine the location of the sensor 120 in the coordinate system of the image. Either way, the processor 151 is configured to overlay the position of the sensor 120 on the image on the monitor 180. For example, a composite image may include the image of the frame (e.g., the last frame) based on imaging beams, and the superposed position of the sensor 120 in that frame providing real-time feedback to a clinician of the position of the sensor 120 and the distal end of the interventional medical device 110 relative to the region of interest. As can be appreciated, the superposing of the position of the sensor 120 may be repeated for each frame to enable complete real-time in-situ superposition of the position of the sensor 120 relative to the composite image of the frame.

Figure 1C:
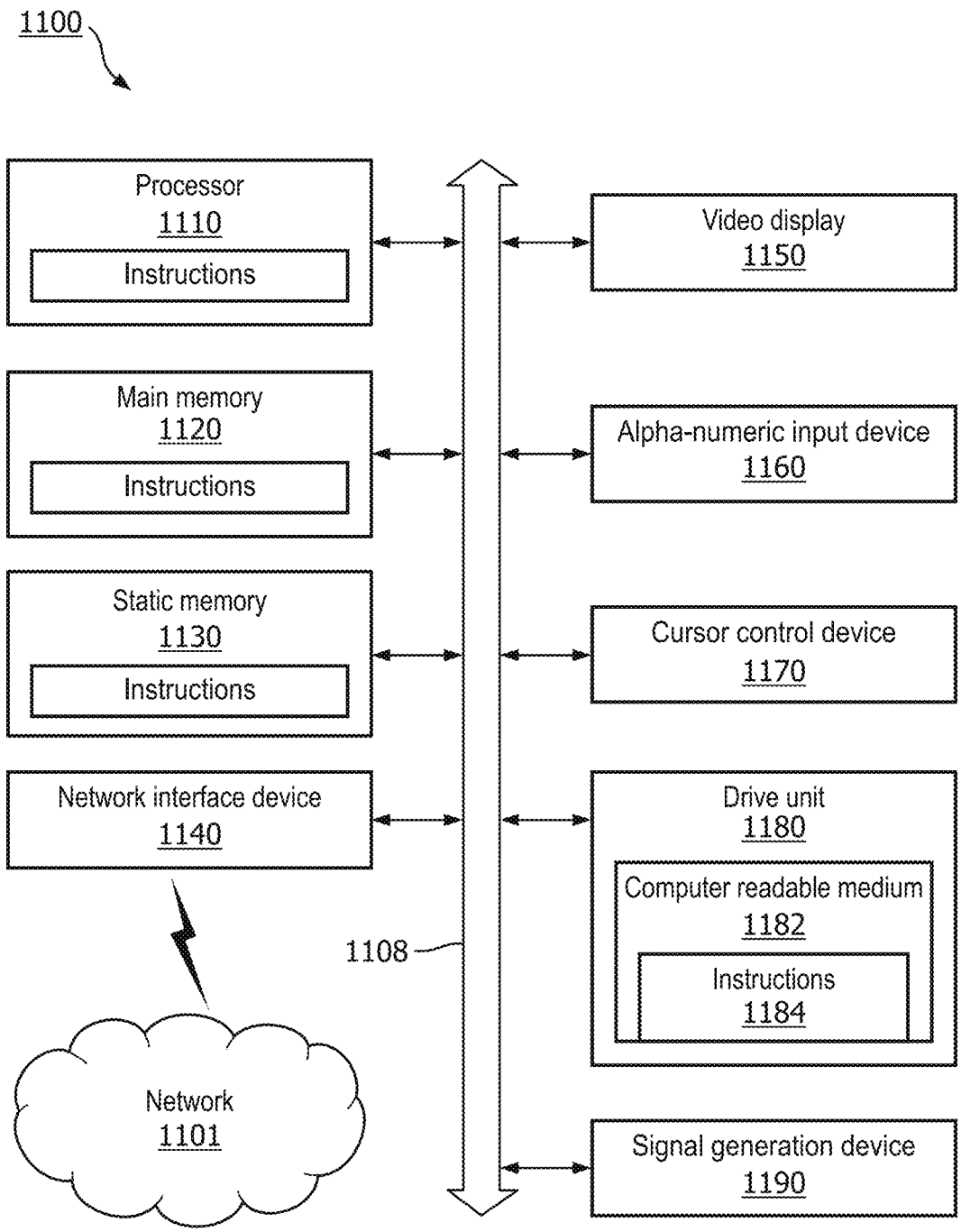
FIG. 1C is an illustrative embodiment of a general computer system, on which a method of interleaved imaging and tracking sequences for ultrasound-based instrument tracking can be implemented, in accordance with a representative embodiment.

FIG. 1C is an illustrative embodiment of a general computer system, on which a method of interleaved imaging and tracking sequences for ultrasound-based instrument tracking can be implemented. The computer system 1100 can include a set of instructions that can be executed to cause the computer system 1100 to perform any one or more of the methods or computer based functions disclosed herein. The computer system 1100 may operate as a standalone device or may be connected, for example, using a network 1101, to other computer systems or peripheral devices. Any or all of the elements and characteristics of the computer system 1100 in FIG. 1C may be representative of elements and characteristics of the central station 150, the imaging probe 130, or even the sensor 120 in FIGS. 1A and 1B.

In a networked deployment, the computer system 1100 may operate in the capacity of a client in a server-client user network environment. The computer system 1100 can also be fully or partially implemented as or incorporated into various devices, such as a control station, imaging probe, image beam receiver, tracking beam receiver, stationary computer, a mobile computer, a personal computer (PC), or any other machine capable of executing a set of instructions (sequential or otherwise) that specify actions to be taken by that machine. The computer system 1100 can be incorporated as or in a device that in turn is in an integrated system that includes additional devices. In an embodiment, the computer system 1100 can be implemented using electronic devices that provide video or data communication. Further, while the computer system 1100 is illustrated, the term "system" shall also be taken to include any collection of systems or sub-systems that individually or jointly execute a set, or multiple sets, of instructions to perform one or more computer functions.

As illustrated in FIG. 1C, the computer system 1100 includes a processor 1110. A processor 1110 for a computer system 1100 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. Any processor described herein is an article of manufacture and/or a machine component. A processor for a computer system 1100 is configured to execute software instructions to perform functions as described in the various embodiments herein. A processor for a computer system 1100 may be a general-purpose processor or may be part of an application specific integrated circuit (ASIC). A processor for a computer system 1100 may also be a microprocessor, a microcomputer, a processor chip, a controller, a microcontroller, a digital signal processor (DSP), a state machine, or a programmable logic device. A processor for a computer system 1100 may also be a logical circuit, including a programmable gate array (PGA) such as a field programmable gate array (FPGA), or another type of circuit that includes discrete gate and/or transistor logic. A processor for a computer system 1100 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 1100 includes a main memory 1120 and a static memory 1130 that can communicate with each other via a bus 1108. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 1100 may further include a video display unit 1150, such as a liquid crystal display (LCD), an organic light emitting diode (OLED), a flat panel display, a solid-state display, or a cathode ray tube (CRT). Additionally, the computer system 1100 may include an input device 1160, such as a keyboard/virtual keyboard or touch-sensitive input screen or speech input with speech recognition, and a cursor control device 1170, such as a mouse or touch-sensitive input screen or pad. The computer system 1100 can also include a disk drive unit 1180, a signal generation device 1190, such as a speaker or remote control, and a network interface device 1140.

In an embodiment, as depicted in FIG. 1C, the disk drive unit 1180 may include a computer-readable medium 1182 in which one or more sets of instructions 1184, e.g. software, can be embedded. Sets of instructions 1184 can be read from the computer-readable medium 1182. Further, the instructions 1184, when executed by a processor, can be used to perform one or more of the methods and processes as described herein. In an embodiment, the instructions 1184 may reside completely, or at least partially, within the main memory 1120, the static memory 1130, and/or within the processor 1110 during execution by the computer system 1100.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 1182 that includes instructions 1184 or receives and executes instructions 1184 responsive to a propagated signal; so that a device connected to a network 1101 can communicate video or data over the network 1101. Further, the instructions 1184 may be transmitted or received over the network 1101 via the network interface device 1140.

Figure 2:
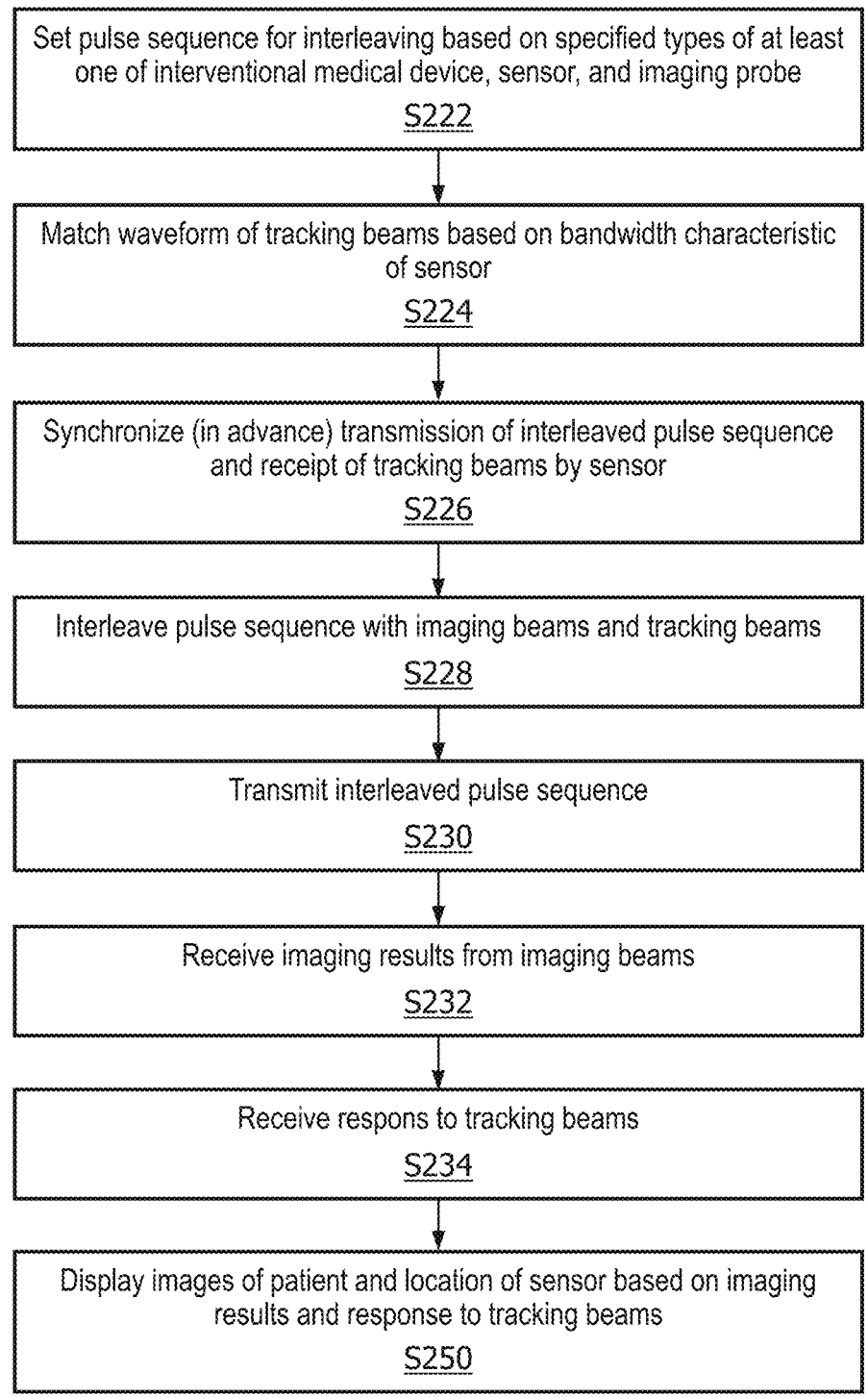
FIG. 2 illustrates a process for interleaved imaging and tracking sequences for ultrasound-based instrument tracking, in accordance with a representative embodiment.

FIG. 2 illustrates a process for interleaved imaging and tracking sequences for ultrasound-based instrument tracking, in accordance with a representative embodiment. In FIG. 2, the process starts at S222 by setting a pulse sequence. The pulse sequence is for interleaving imaging beams and tracking beams. At S222, the pulse sequence is set based on specified types of the interventional medical device 110, the sensor 120, and/or the imaging probe 130. Accordingly, pulse sequences to use may vary by different types of the interventional medical device 110, the sensor 120, and/or the imaging probe 130, and at S222 the pulse sequence can be set by, for example, inputting or detecting which types are being used.

At S224, a waveform of the tracking beams is matched based on a bandwidth characteristic of the sensor 120. That is, different types of sensor 120 will have different bandwidth characteristics, and a waveform of the tracking beams can be matched based on the bandwidth characteristic.

At S226, transmission of the interleaved pulse sequence and receipt of the tracking beams by the sensor 120 is synchronized in advance. That is, the expected timing patterns are established in advance, since the receipt of the tracking beams is the intended purpose of the interleaving by the ultrasound system 100. Accordingly, a transmit/receive/transmit/receive timing sequence for transmitting the interleaved pulse sequence and receiving the tracking beams by the sensor 120 is established in advance.

At S228, the pulse sequence is interleaved with the imaging beams and the tracking beams. Several examples of specific interleaving patterns will be described herein with respect to FIGS. 6A and 6B.

At S230, the interleaved pulse sequence is transmitted. From FIGS. 1A and 1, the imaging probe 130 emits the interleaved pulse sequence, and the interventional medical device 110 and the sensor 120 receive the interleaved pulse sequence. The imaging beams of the interleaved pulse sequence will result in imaging results being detected by the imaging probe 130. Indeed, the synchronization at S226 is in anticipation of the tracking beams being received by the sensor 120, whereas the reflected imaging beams are alternately received by the imaging probe 130.

At S234, a response to the tracking beams is received. The tracking beams are different than the imaging beams in most circumstances described herein, such as when the tracking beams have waveforms matched based on bandwidth characteristics of the sensor 120. As noted throughout this disclosure, the tracking beams result in tracking location of the sensor 120 and the interventional medical device 110 in the patient.

At S250, images of the patient are displayed based on the imaging results, and location of the sensor 120 is displayed based on the response to the tracking beams. Accordingly, the location of the sensor 120 may be displayed as, for example, a bright spot on an ultrasound image to show approximately or exactly where the sensor 120 is relative to the patient.

Figure 3:
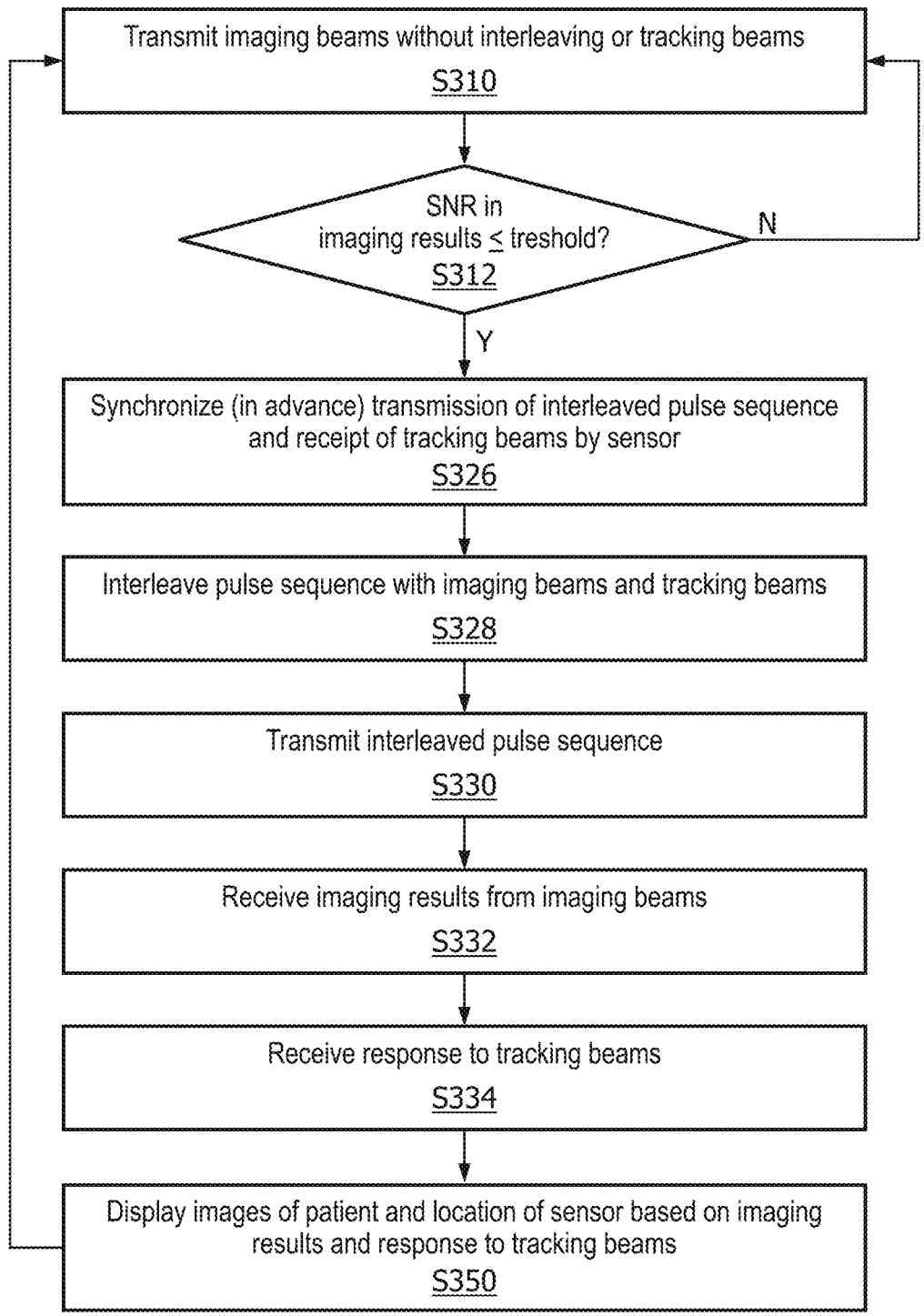
FIG. 3 illustrates another process for interleaved imaging and tracking sequences for ultrasound-based instrument tracking, in accordance with a representative embodiment.

FIG. 3 illustrates another process for interleaved imaging and tracking sequences for ultrasound-based instrument tracking, in accordance with a representative embodiment. In FIG. 3, imaging beams are initially transmitted without interleaving or tracking beams at S310. In the embodiment of FIG. 3, the tracking using tracking beams is only selectively used as explained herein.

At S312, a check is made whether a signal-to-noise ratio in the imaging beams received by the sensor 120 is below a predetermined threshold. If the signal-to-noise ratio is above the threshold (S312=No), the process continues in a loop without using the tracking beams or interleaving. In other words, an ultrasound can be used in a conventional manner unless and until a signal-to-noise ratio in the imaging beams received by the sensor 120 is below a predetermined threshold, and the imaging beams are then used for tracking purposes in a one-way configuration. Tracking beams are enabled when, for example, the signal-to-noise ratio reflects that the interventional medical device 110 and sensor 120 may not be where they are supposed to as shown by an unexpectedly low signal-to-noise ratio from the imaging beams received by the sensor 120. In another embodiment, signal-to-noise levels in imaging results based on the echo received by the imaging probe 130 may also or alternatively be used to determine when to selectively begin using tracking beams.

At S326, transmission of the interleaved pulse sequence is synchronized with receipt of the tracking beams by the sensor 120, and at S328 the imaging beams and tracking beams are interleaved in the pulse sequence. At S330 the interleaved pulse sequence is transmitted, and at S332, the imaging results are received from the imaging beams, and at S334 the response to the tracking beams is received. At S350, images of the patient and location of the sensor 120 are displayed based on the imaging results and the response to the tracking beams. In other words, the process from S326 to S350 is the same as the process from S226 to S250. However, at S350, the process reverts to transmitting imaging beams without interleaving or tracking beams at S310, to see if the signal-to-noise ratio has improved such that location of the sensor 120 can be reliably established using imaging beams only as in the prior art, for the time being. If the signal-to-noise ratio in the imaging beams received at sensor 120 (and, optionally, pulse-echo signal-to-noise ratio from the imaging beams) is again below the threshold at S312, the process will resume using the interleaving and the tracking beams.

Figure 4:
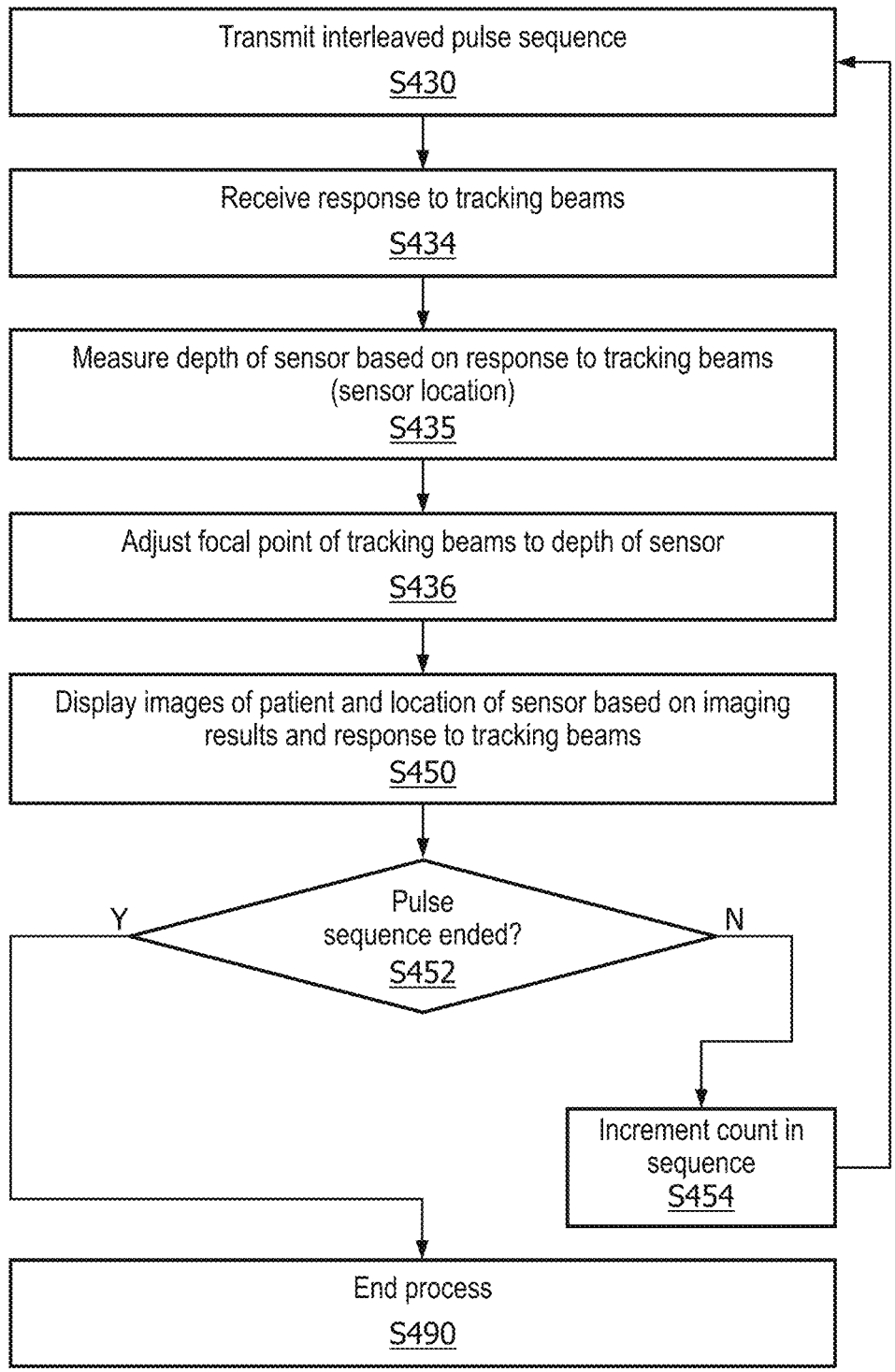
FIG. 4 illustrates another process for interleaved imaging and tracking sequences for ultrasound-based instrument tracking, in accordance with a representative embodiment.

FIG. 4 illustrates another process for interleaved imaging and tracking sequences for ultrasound-based instrument tracking, in accordance with a representative embodiment. In FIG. 4, the process begins at S430 by transmitting an interleaved pulse sequence. At S434, the response to tracking beams is received, and at S435 the process measures the depth of the sensor 120 based on the response to the tracking beams. In other words, the depth of the sensor 120 is measured based on the location of the sensor 120 derived from the response to the tracking beams.

At S436, a focal point of the tracking beams is adjusted to the depth of the sensor 120 measured at S435. At S450, images of the patient and the location of the sensor 120 are displayed based on the imaging results and the response to the tracking beams. At S452, a check is made whether the pulse sequence has ended, and if so (S452=Yes) the process ends at S490. If the pulse sequence has not ended (S452=No), a count of the sequence is incremented at S454, and the process returns to transmitting the interleaved pulse sequence at S430.

The process of FIG. 4 shows two aspects to be noted. The first is that a focus point of the tracking beams may be matched to the depth of the sensor 120. The second is that the sequence may be tracked by counting, e.g., imaging frames, tracking frames, imaging/tracking super-frames, and other characteristics of the pulse sequence. The count at S454 can be used to track an end to the pulse sequence when sub-processes such as adjusting focal points are performed.

Figure 5A:
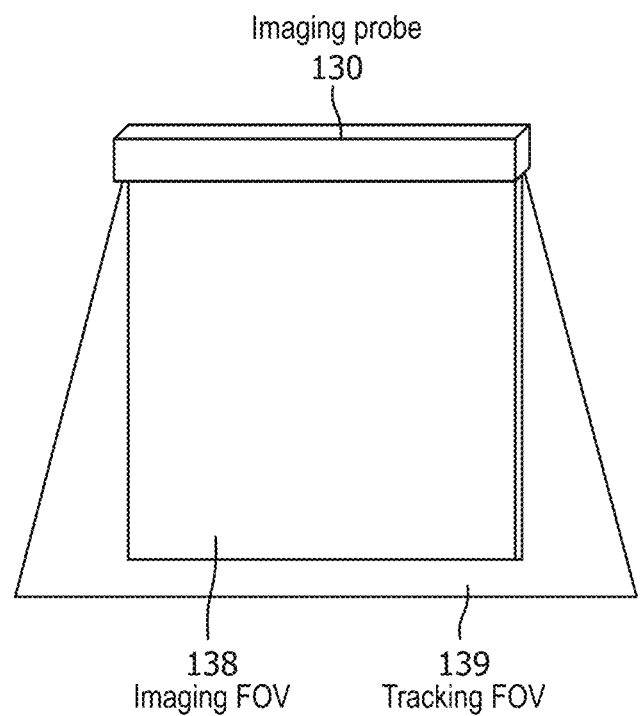
FIG. 5A illustrates relative fields of view from an imaging probe in an embodiment of interleaved imaging and tracking sequences for ultrasound-based instrument tracking, in accordance with a representative embodiment.

FIG. 5A illustrates relative fields of view from an imaging probe in an embodiment of interleaved imaging and tracking sequences for ultrasound-based instrument tracking, in accordance with a representative embodiment. In FIG. 5A, the imaging probe 130 emits imaging beams in an imaging field of view 138, and tracking beams in a tracking field of view 139. As can be seen, the tracking field of view 139 extends beyond the imaging field of view 138. The tracking field of view 139 shows that tracking beams can be directed in directions to which the imaging beams are not directed, which means that the sensor 120 can be located even when the interventional medical device is not in the imaging field of view 139 and will not appear in the images. FIG. 5A is applicable to a two-dimensional (2D) probe, for example. When tracking is performed exclusively using imaging beams, tracking of the sensor 120 is limited to the imaging field of view. However, as shown in FIGS. 5A and 5B it will be possible to track outside of the imaging field of view using separate tracking beams.

For example, tracking outside of the imaging field of view may be useful for guiding needles with two-dimensional (2D) curvilinear or linear probes, wherein using only imaging beams the guiding needle is not visible until a few centimeters into tissue. In another example, tracking a needle out of a plane may be useful even when only a plane is being imaged using a 2D array. For the needle guidance example, the tracking beams can be extended to cover a larger field of view by steering. For out of plane tracking, a tracking volume can be used even when only a plane is being imaged using the 2D array.

Figure 5B:
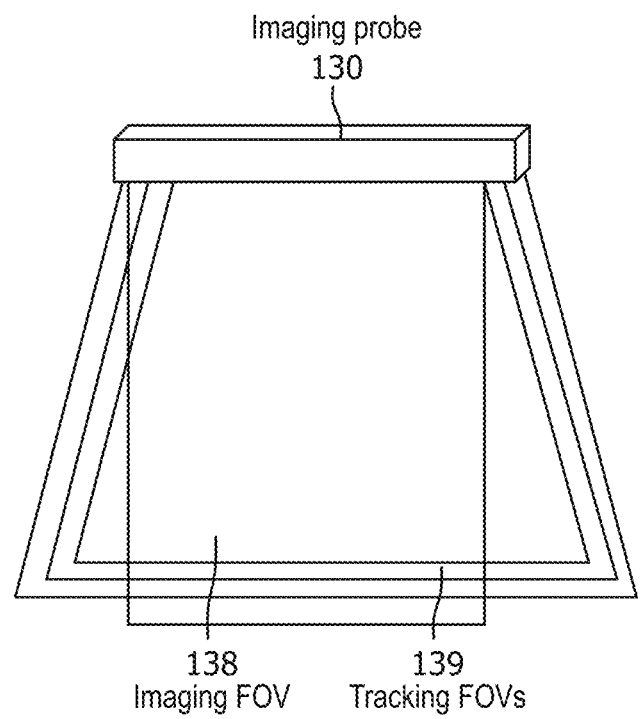
FIG. 5B illustrates relative fields of view from an imaging probe in another embodiment of interleaved imaging and tracking sequences for ultrasound-based instrument tracking, in accordance with a representative embodiment.

FIG. 5B illustrates relative fields of view from an imaging probe in another embodiment of interleaved imaging and tracking sequences for ultrasound-based instrument tracking, in accordance with a representative embodiment. In FIG. 5B, multiple tracking fields of view 139 are shown for a single imaging field of view 138. FIG. 5B is applicable to a three-dimensional (3D) probe, for example.

A frame rate of imaging beams is reduced when imaging beams and tracking beams are interleaved. Accordingly, the frame rates of each of the imaging beams and tracking beams can be optimized. The optimization of tracking beam characteristics may allow for interleaving a single tracking sequence with multiple or all so-called imaging tissue-specific presets (TSPs) which are preset imaging settings specific to particular tissues. This, in turn, eliminates any requirement to transmit many beam parameters from a scanning module to a tracking module.

As a general matter, resolution for tracking beams does not have to be as high as for imaging beams, as only a spatial peak is sought in the received signals of the tracking beams. The tracking performance is better characterized in terms of accuracy than resolution, and resolution only secondarily affects accuracy. In other words, performance of the existing use exclusively of imaging beams is dependent on the shape and density of transmit imaging beams, but the dependency is not straightforward and is affected by the processing algorithms to obtain position from signals of the tracking beam. Therefore, in general, lower-resolution transmit beams (i.e., broad beams) can be used to maintain frame rate.

Additionally, transmit beam reconstruction can be performed on received signals to improve resolution. Ultrafast tracking sequences with plane waves or diverging beams can therefore be used to improve tracking frame rate. Conversely, if sensitivity of tracking is to be optimized, an oversampled transmit beam sequence may be used to enhance a signal-to-noise ratio.

To maximize tracking sensitivity, a waveform of the tracking beams can be matched to a bandwidth characteristic of the sensor 120 aboard the interventional medical device 110. For instance, if an interventional medical device 110 is a needle, and a sensor 120 has a 5 MHz characteristic, the tracking signal-to-noise ratio will vary widely between preset settings for different tissues, where imaging frequencies can range from 4 to 7 MHz. In addition, tracking beams suited for "penetration" may use a larger number of cycles, lower frequency, and coded excitation. Such tracking beams can be repeated or strongly overlapped to maximize signal-to-noise ratio. Empirical observations reveal that these waveform changes typically benefit tracking more in sensitivity improvements than in degradation of accuracy. Since the tracking may be limited to searching for a spatial peak in received data, accuracy may be sacrificed as a secondary concern compared to imaging resolution.

As noted with respect to FIG. 4, tracking beams can also be focused at the depth of the sensor 120 by, e.g., measuring the sensor depth by tracking the sensor location with ultrasound imaging beams and feeding this information back to the transmit beamformer. By focusing tracking beams at the depth of the sensor 120, signal-to-noise ratio and accuracy can be maximized for tracking. Moreover, the focal depth for tracking frames can be maintained independent of a transmit focal depth for the imaging frames, so that it may be preferable to independently set focus depth for each of imaging and for tracking.

In an embodiment, frame interleave can be used, wherein one or more imaging frames are interleaved with one or more tracking frames. However, frame interleave may introduce lag between imaging frames and tracking frames, which may be detectable at very low imaging/tracking rates (<10 Hz). When beam interleave is alternatively used, imaging beams are interleaved with tracking beams within a frame. Frame interleave versus beam interleave are illustrated and explained more below in FIGS. 6A and 6B. Using either frame interleave or beam interleave, a ratio of imaging frames to tracking frames or imaging beams to tracking beams can be adapted.

FIG. 6A illustrates a timing diagram for an embodiment of interleaved imaging and tracking sequences for ultrasound-based instrument tracking, in accordance with a representative embodiment. FIG. 6A shows an example of frame interleave. In FIG. 6A, an imaging frame 605 and a tracking frame 610 are alternatively and sequentially emitted in a pulse sequence. The imaging beams in the imaging frame 605 are shown thinner than the tracking beams in the tracking frame 610. As shown, the horizontal axis is in the time dimension, so the sequential emission of imaging frame 605, tracking frame 610, imaging frame 605, tracking frame 610, is sequential in the time dimension.

FIG. 6B illustrates a timing diagram for another embodiment of interleaved imaging and tracking sequences for ultrasound-based instrument tracking, in accordance with a representative embodiment. FIG. 6B shows an example of beam interleave. In FIG. 6B, an imaging/tracking superframe 655 is followed by another imaging/tracking superframe 665. Again, the horizontal axis is in the time dimension, so the sequential emission of imaging/tracking superframe 655, imaging/tracking superframe 665 is sequential in the time dimension. Each of the imaging/tracking superframes 655, 665 includes alternating sequences of two imaging beams, one tracking beam, two imaging beams, one tracking beam.

To lessen the impact from tracking beams on frame rate, tracking beams might only be transmitted in a sub-region of an imaging volume surrounding an expected location of sensor 120. An expected location of sensor 120 can be based on historical positions of the sensor 120, or by processing sensor data from the imaging beams. Data from the imaging frame can be used to provide a coarse position estimate that is refined using tracking beams.

Additionally, to lessen the impact from tracking beams on frame rate, the tracking beams can be restricted to directions where imaging beams are not already being sent. For example, in the extended field of views in FIGS. 5A and 5B, additional beams could be restricted beyond a normal to the surface where the imaging field of view does not overlap the tracking field of view.

Most embodiments described herein use tracking frames and interleaving. However, the use of tracking beams and/or interleaving can be selectively activated as a back-up when, for instance, imaging beams are used for tracking as a default. Examples of this are described below, and the embodiment of FIG. 7 describes such selective use of tracking beams.

Alternatively, the interleaved imaging beams and tracking beams can each, separately, be used to track the sensor 120 aboard the interventional medical device 110. Using both the interleaved imaging beams and tracking beams separately has the advantage that tracking frame rate is not lost whereas additional measurements that may either be in an expanded field of view or with more sensitivity are affirmatively gained. High-confidence measurements of tracking beams and lower confidence measurements of imaging beams can be used in several ways. For instance, a low-pass or Kalman filter can be used across beams or frames as a filter. The Kalman filter can weight the measurements of tracking beams more than the measurements of imaging beams. Similarly, a tool trajectory can be modeled, and the model can be constrained with the measurements of tracking beams and estimates of the error of the model on all measurements. Different modalities can be used to remove artefacts from the measurements of the imaging beams. For instance, if the positions computed for the imaging and tracking measurements differ too much, the maximum peak in the imaging results can be used in a region seeded by the measurements of the tracking beams.

When the field of view is expanded, some instances of the measurements based on tracking beams may result in a confident estimate when the measurements based on imaging beams are just noisy. In these cases, measurements from the imaging beams are discarded. The discarding may be based on a threshold of signal-to-noise ratio. For example, a high signal-to-noise ratio in the measurements of tracking beams and a lower signal-to-noise ratio in the measurements of imaging beams likely reflects that the sensor 120 is in the tracking field of view but outside the imaging field of view.

Figure 7:
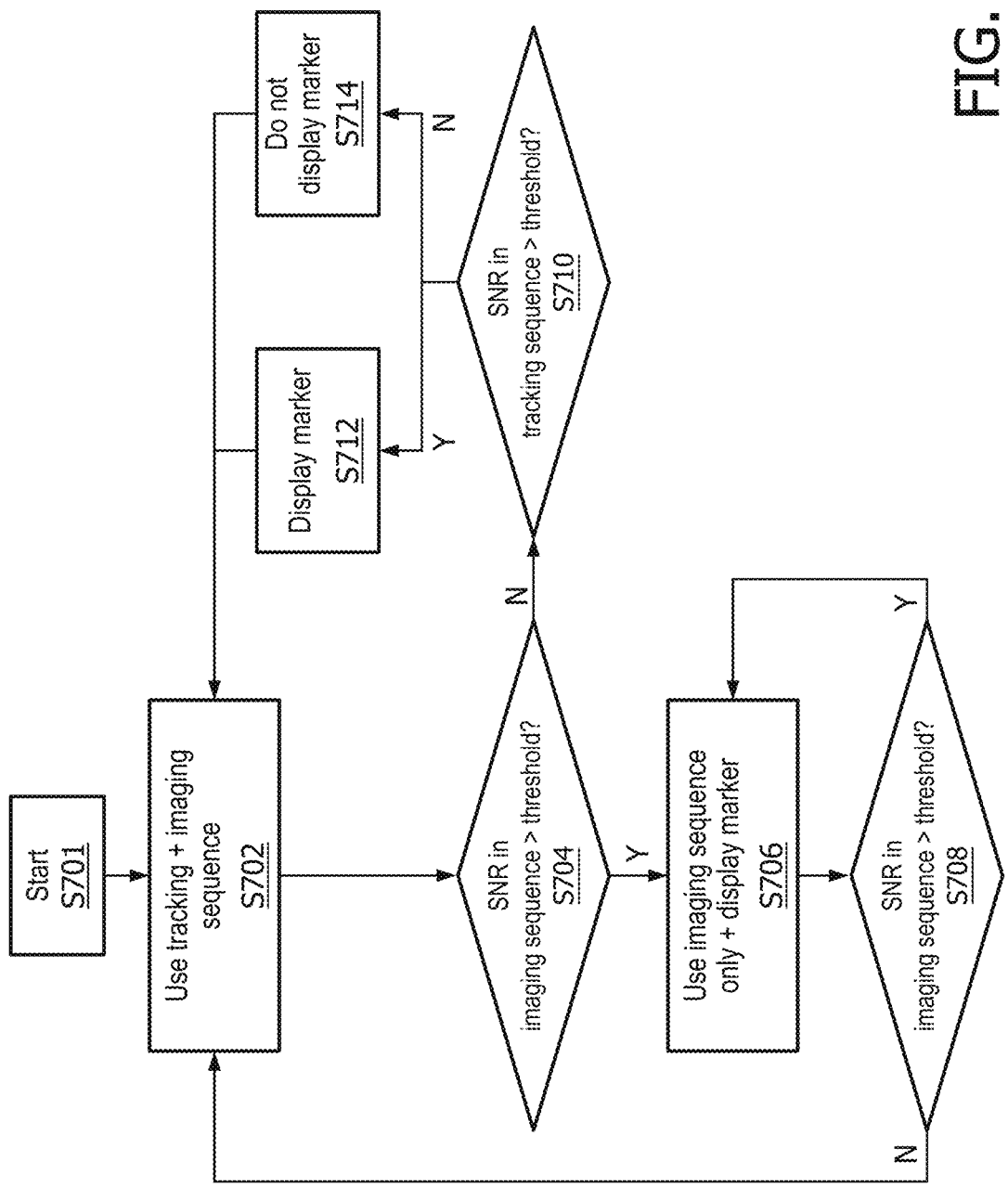
FIG. 7 illustrates another process for interleaved imaging and tracking sequences for ultrasound-based instrument tracking, in accordance with a representative embodiment.

FIG. 7 illustrates another process for interleaved imaging and tracking sequences for ultrasound-based instrument tracking, in accordance with a representative embodiment. In the embodiment of FIG. 7, an expanded field of view using high sensitivity tracking beams or frames may be activated only when the measurements based on imaging results reflect a low signal-to-noise ratio suggesting that the signals of the imaging beams have been effectively lost. The low signal-to-noise ratio results in a signal being sent to the system for tracking the interventional medical device to start searching for the sensor 120, i.e., to activate the tracking beams/frames. This results in a trade-off in that the imaging frame rate is temporarily lowered, but this will last only until the sensor 120 is found again and returned into the field of view for the imaging beams. When the sensor 120 is found again and returned into the field of view for the imaging beams, special tracking frames are turned off and tracking returns to the default of using only the imaging beams. When the imaging signal-to-noise drops again, the use of tracking beams or frames is selectively restarted.

In FIG. 7, the process starts at S701. At S702, a pulse sequence with tracking beams and imaging beams is used. At S704, a check is made whether the signal-to-noise ratio in the imaging results (i.e., from the imaging beams) is above a threshold. If the signal-to-noise ratio is above the threshold (S704=Yes), only the imaging sequence is emitted, along with a display marker at S706. The imaging sequence and display marker are repeatedly emitted until the signal-to-noise ratio falls back below the threshold in a check at S708, at which time the tracking beams and imaging beams are used.

At S704, if the signal-to-noise ratio is not above the threshold when using the tracking beams and imaging beams (S704=No), a check is made for the signal-to-noise ratio in the tracking sequence at S710. If the signal-to-noise in the tracking sequence is above a threshold (S710=Yes), a marker is displayed at S712 and the process returns to S702. If the signal-to-noise in the tracking sequence is not above the threshold at S710 (S710=No), no marker is displayed at S714, and the process returns to using tracking beams and imaging beams at S702.

According to the embodiment of FIG. 7, tracking and imaging are used until the signal-to-noise in the imaging sequence falls below a threshold at S704 or S708. Additionally, the process checks if signal-to-noise in the tracking sequence is below a threshold if the signal-to-noise ratio is below the threshold at S704, so not even a marker for the sensor 120 is displayed if the signal-to-noise in both the imaging sequence (S704=No) and the tracking sequence (S710=No) are both too low.

The embodiment of FIG. 7 represents an efficient use of tracking beams in an interleaved pulse sequence. The selective use of tracking beams is activated only when the imaging sequence is not able to detect the sensor 120. The embodiment of FIG. 7 therefore helps put an interventional medical device 110 and sensor 120 back into the field of view.

Figure 8A:
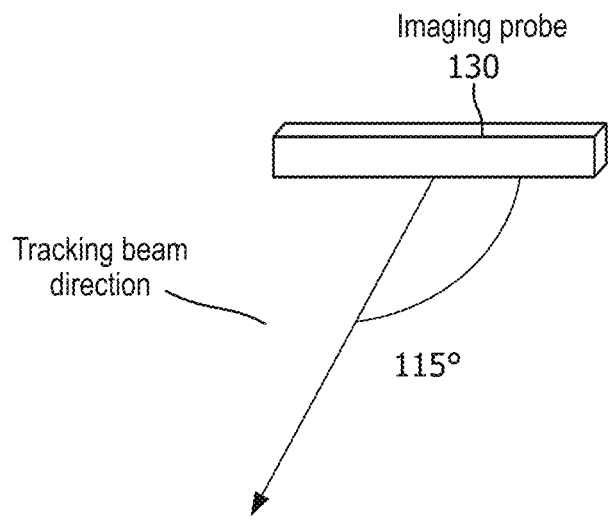
FIGS. 8A-8C illustrate relative directionality for tracking beams and imaging beams for interleaved imaging and tracking sequences for ultrasound-based instrument tracking, in accordance with a representative embodiment.
Figure 8B:
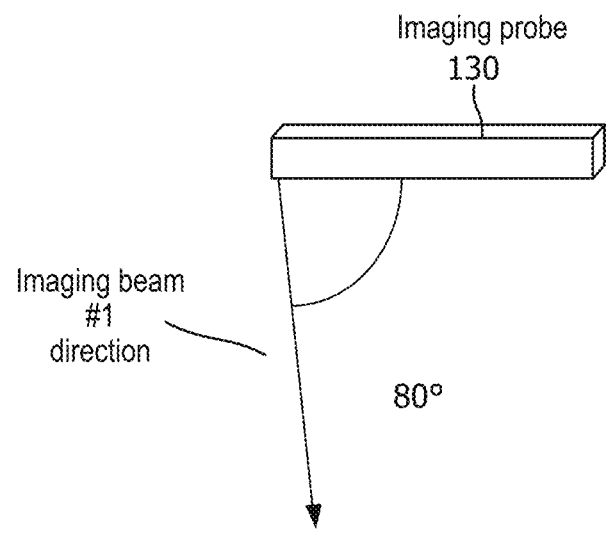
Figure 8C:
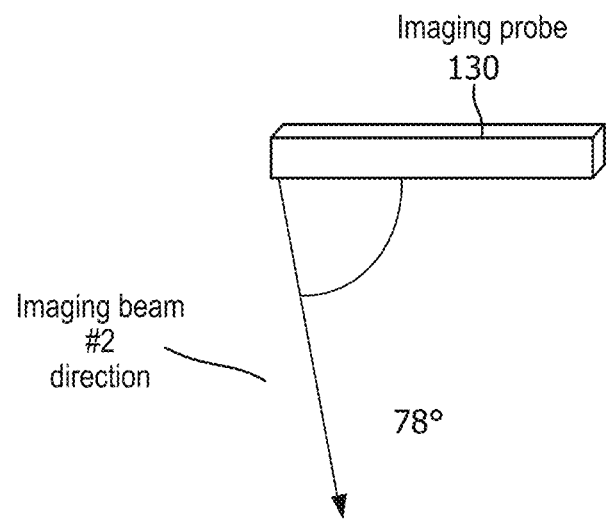

FIGS. 8A-8C illustrate relative directionality for tracking beams and imaging beams for interleaved imaging and tracking sequences for ultrasound-based instrument tracking, in accordance with a representative embodiment. In FIG. 8A, an imaging probe 130 emits a tracking beam in a direction 1150 below horizontal clockwise. In FIG. 8B, the imaging probe 130 emits a first imaging beam in a direction of 80° below horizontal clockwise. In FIG. 8C, the imaging probe 130 emits a second imaging beam in a direction of 78° below horizontal clockwise. In other words, FIGS. 8A-8C illustrate that tracking beams and imaging beams may be centered in different directions, even 20° or more apart. The divergence in directions of tracking beams and imaging beams may be for even immediately adjacent/sequential emissions of the tracking beams and imaging beams.

Figure 9A:
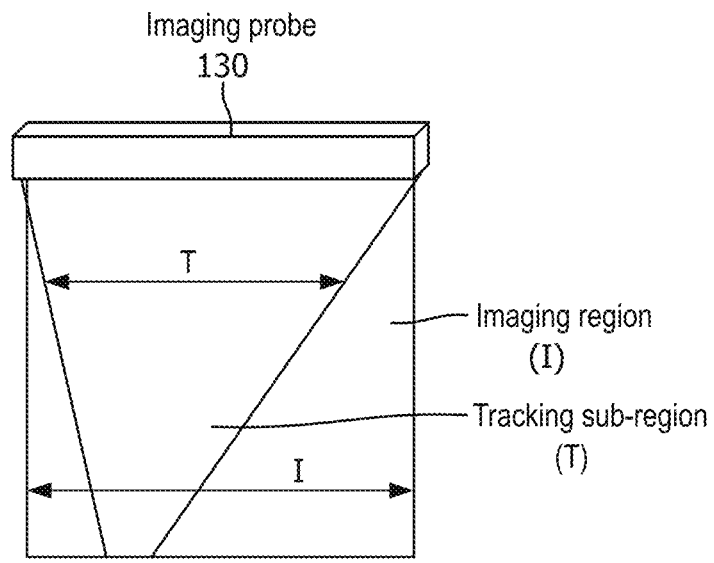
FIG. 9A illustrate relative regions for imaging and tracking from an imaging probe in an embodiment of interleaved imaging and tracking sequences for ultrasound-based instrument tracking, in accordance with a representative embodiment.

FIG. 9A illustrate relative regions for imaging and tracking from an imaging probe in an embodiment of interleaved imaging and tracking sequences for ultrasound-based instrument tracking, in accordance with a representative embodiment. In FIG. 9A, an imaging region is shown to extend entirely below the imaging probe 130, whereas the tracking region is shown to extend within a sub-region of the imaging region. In FIG. 9A the tracking sub-region is to the left side of the imaging region.

Figure 9B:
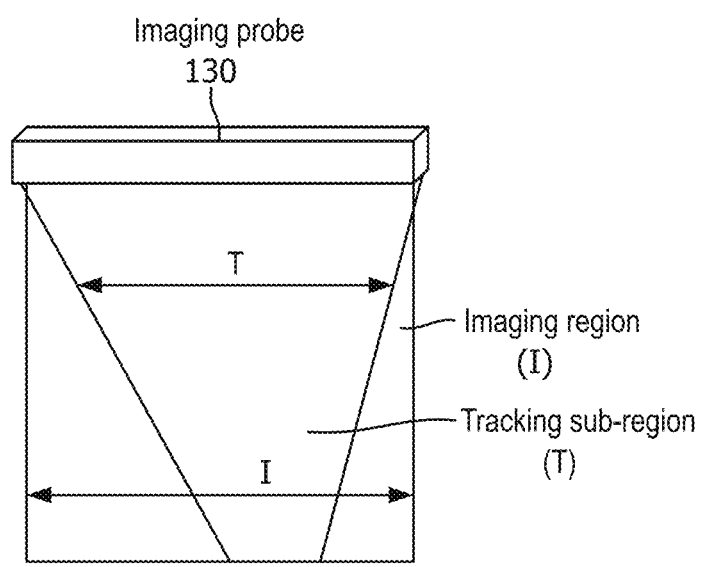
FIG. 9B illustrates relative regions for imaging and tracking from an imaging probe in another embodiment of interleaved imaging and tracking sequences for ultrasound-based instrument tracking, in accordance with a representative embodiment.

FIG. 9B illustrates relative regions for imaging and tracking from an imaging probe in another embodiment of interleaved imaging and tracking sequences for ultrasound-based instrument tracking, in accordance with a representative embodiment. In FIG. 9B, an imaging region is shown to extend again entirely below the imaging probe 130, whereas the tracking region is shown to extend again within a sub-region of the imaging region but to the right side of the imaging region.

Figure 10A:
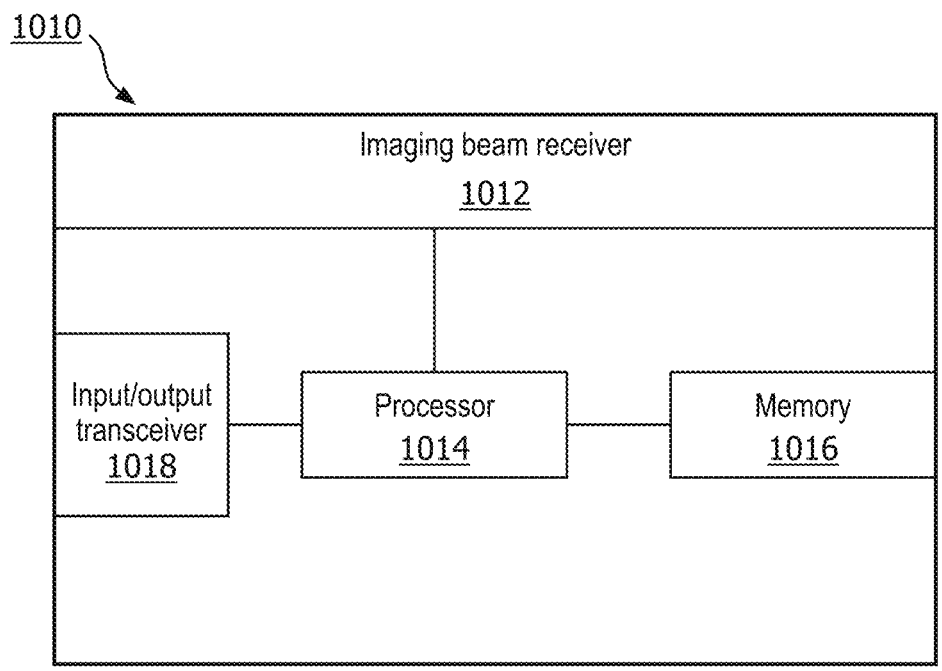
FIG. 10A illustrates a block diagram of an interventional medical device for interleaved imaging and tracking sequences, in accordance with a representative embodiment.

FIG. 10A illustrates a block diagram of an interventional medical device for interleaved imaging and tracking sequences, in accordance with a representative embodiment. In FIG. 10A, the interventional medical device 1010 includes an image beam receiver 1012, an input/output transceiver 1018, a processor 101 and a memory 1016. In FIG. 10A, the interventional medical device 1010 is therefore a logical device. However, in almost all embodiments described herein, an interventional medical device 1010 does not have to be a logical device, and may instead be a simple needle etc.

Figure 10B:
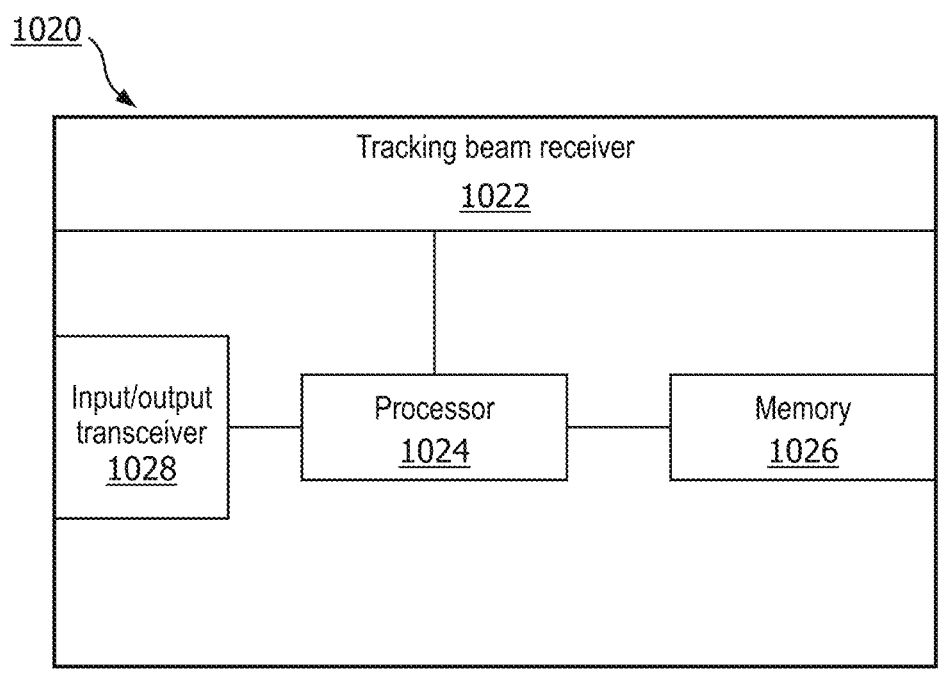
FIG. 10B illustrates a block diagram of a sensor for interleaved imaging and tracking sequences, in accordance with a representative embodiment.

FIG. 10B illustrates a block diagram of a sensor for interleaved imaging and tracking sequences, in accordance with a representative embodiment. In FIG. 10B, the sensor 1020 includes a tracking beam receiver 1022, an input/output transceiver 1028, a processor 1024, and a memory 1026. In FIG. 10B, the sensor 1020 is therefore a logical device. A sensor 1020 may be either passive or active, in that the sensor 1020 may passively reflect received tracking beams to respond to the tracking beams, or may actively process received tracking beams and logically generate a response to the received tracking beams. If the sensor 1020 is a logical device, the processor 1024 may execute instructions stored in the memory 1026, to respond to received tracking beams using the input/output transceiver 1028.

Accordingly, interleaved imaging and tracking sequences for ultrasound-based instrument tracking enables optimal tracking of sensor 120. Optimization can be varied for interventional medical devices 110 that differ, such as needles, catheters, and guidewires etc. Optimization can also be varied for different types of sensor 120, such as piezoelectric (PZT), polyvinylidene difluoride (pvdf). In an embodiment, multiple tracking beam or frame parameters can be programmed into an ultrasound system, for example as tracking frame parameter set #1, tracking parameter set #2. Accordingly, sensor specific presets can be defined for an ultrasound system, analogous to tissue specific presets (TSPs) for tissue imaging. A user can be allowed to choose a desired tracking frame parameter set as a sensor specific preset (SSP) to use for a given combination of imaging probe 130, interventional medical device 110, and sensor 120. For example, if the tracked interventional medical device 110 is a guidewire, the sensor 120 is PZT and optimized for 12 MHz, and the imaging probe 130 is a linear probe L12-5, the tracking parameter set programmed for the highest frequency setting (closest to 12 MHz) can be used. The user choice for tracking settings can be provided, for example, via an ultrasound system user interface next to a button for tissue specific presets.

Although interleaved imaging and tracking sequences for ultrasound-based instrument tracking has been described with reference to several exemplary embodiments, it is understood that the words that have been used are words of description and illustration, rather than words of limitation. Changes may be made within the purview of the appended claims, as presently stated and as amended, without departing from the scope and spirit of interleaved imaging and tracking sequences for ultrasound-based instrument tracking in its aspects. Although interleaved imaging and tracking sequences for ultrasound-based instrument tracking has been described with reference to particular means, materials and embodiments, interleaved imaging and tracking sequences for ultrasound-based instrument tracking is not intended to be limited to the particulars disclosed; rather interleaved imaging and tracking sequences for ultrasound-based instrument tracking extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover all subsequent adaptations or variations of various embodiments. Combinations of the above embodiments, and other embodiments not specifically described herein, will be apparent to those of skill in the art upon reviewing the description.

As described above, ultrasound-based tracking of instruments can be enhanced by using separate tracking beams. As described herein, signal-to-noise ratios can be enhanced, and a larger field of view obtained that is especially useful for linear arrays and in-plane insertions. The field of view can also be enhanced in the elevation direction for in-plane and out-of-plane needle insertions.

According to an aspect of the present disclosure, a method for tracking an interventional medical device in a patient includes interleaving, by an imaging probe external to the patient, a pulse sequence of imaging beams and tracking beams to obtain an interleaved pulse sequence. The method also includes transmitting, from the imaging probe to the interventional medical device in the patient, the interleaved pulse sequence. The method further includes determining, based on a response to the tracking beams received from a sensor on the interventional medical device, a location of the sensor in the patient.

According to another aspect of the present disclosure, the method further includes receiving imaging results based on the imaging beams.

According to yet another aspect of the present disclosure, the method also includes synchronizing transmitting of the interleaved pulse sequence and receiving of the tracking beams by the sensor.

According to still another aspect of the present disclosure, the method includes displaying, on a monitor, images of the patient based on the imaging results and the location of the sensor in the patient based on the response to the tracking beams.

According to another aspect of the present disclosure, the method further includes providing, by the sensor, the response to the tracking beams.

According to yet another aspect of the present disclosure, the interleaved pulse sequence is interleaved in time segments.

According to yet another aspect of the present disclosure, the method includes displaying, on a monitor, multiple, successive locations of the sensor based on the tracking beams as the imaging probe is moved in the patient.

According to still another aspect of the present disclosure, characteristics of the imaging beams including at least one of shape, position, and waveform, differ from characteristics of the tracking beams.

According to another aspect of the present disclosure, the pulse sequence comprises a single tracking beam sequence and multiple different pre-set imaging beam sequences that vary based on specific tissues being imaged.

According to yet another aspect of the present disclosure, the method also includes matching a waveform of the tracking beams to a bandwidth characteristic of the sensor.

According to still another aspect of the present disclosure, the method further includes measuring a depth of the sensor; and focusing the tracking beams at the depth of the sensor.

According to another aspect of the present disclosure, the sensor is tracked outside a field of view of the imaging beams.

According to yet another aspect of the present disclosure, the interleaving comprises interleaving at least one imaging frame with at least one tracking frame.

According to still another aspect of the present disclosure, the interleaving includes interleaving the imaging beams and tracking beams within a frame.

According to another aspect of the present disclosure, the transmitting further includes transmitting the imaging beams in a region of the patient, and transmitting the tracking beams only in a sub-region of the region based on projecting expected positions of the sensor from historical sensor positions.

According to yet another aspect of the present disclosure, the transmitting includes transmitting the imaging beams in a region of the patient, and transmitting the tracking beams only in a sub-region of the region based on processing imaging data from the imaging beams.

According to still another aspect of the present disclosure, the transmitting includes transmitting the imaging beams in at least one first direction, and transmitting the tracking beams in a second direction different than any at least one first direction.

According to another aspect of the present disclosure, the interleaved pulse sequence is selectively sent based on relative signal-to-noise measurements determined from the imaging beams received by the sensor.

According to yet another aspect of the present disclosure, the interleaved pulse sequence varies based on a combination of types of the interventional medical device, sensor and imaging probe.

According to an aspect of the present disclosure, a system for tracking an interventional medical device in a patient include an imaging probe and a sensor. The imaging probe is external to the patient and interleaves a pulse sequence of imaging beams and tracking beams to obtain an interleaved pulse sequence. The imaging probe also transmits the interleaved pulse sequence to the interventional medical device in the patient. The sensor is on the interventional medical device and responds with a response to the tracking beams from the imaging probe. The system determines, based on the response to the tracking beams, a location of the sensor in the patient.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive patient matter may be directed to less than all the features of any of the disclosed embodiments. Thus, the following claims are incorporated into the Detailed Description, with each claim standing on its own as defining separately claimed patient matter.

The preceding description of the disclosed embodiments is provided to enable any person skilled in the art to practice the concepts described in the present disclosure. As such, the above disclosed patient matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for tracking a sensor, the system comprising:
 a sensor configured to receive ultrasound tracking beams and transmit a response to the ultrasound tracking beams; and
 a processor communicatively coupled to an imaging probe, the processor configured to:
  interleave a pulse sequence of ultrasound imaging beams and the ultrasound tracking beams to obtain an interleaved pulse sequence,
  synchronize transmission of the interleaved pulse sequence and receipt of the ultrasound tracking beams by the sensor based on establishing a timing pattern for the transmission of the interleaved pulse sequence and the receipt of the ultrasound tracking beams,
  transmit the interleaved pulse sequence to the sensor, and
  based on the response to the ultrasound tracking beams from the sensor, determine a location of the sensor.

2. The system of claim 1, wherein the processor is further configured to:
 generate an image of a region of a patient based on the ultrasound imaging beams;
 display the image and the determined location of the sensor in the image.

3. The system of claim 1, wherein the interleaved ultrasound imaging beams and ultrasound tracking beams are interleaved within a frame.

4. The system of claim 1, wherein the processor is further configured to:
 transmit the ultrasound imaging beams in a region of a patient, and
 transmit the ultrasound tracking beams only in a sub-region of the region based on: (i) projecting expected positions of the sensor determined based on historical sensor positions or (ii) processing imaging data from the ultrasound imaging beams.

5. The system of claim 1, wherein the interleaved pulse sequence comprises a single tracking beam sequence and multiple different imaging beam sequences that vary based on tissue type being imaged.

6. The system of claim 1, wherein the processor is further configured to:
measure a depth of the sensor; and
focus the ultrasound tracking beams at the depth of the sensor.

7. The system of claim 1, wherein the processor is further configured to:
based on the response to the ultrasound imaging beams received from the sensor, determine signal-to-noise measurements, and
select to enable or disable transmission of the interleaved pulse sequence based on the signal-to-noise measurements.

8. The system of claim 1, wherein: the imaging probe is positioned external to the patient; and the sensor is disposed on an interventional medical device, and configured to be positioned in the patient.

9. A non-transitory computer-readable storage medium having stored a computer program comprising instructions, which, when executed by a processor, cause the processor to:
interleave a pulse sequence of ultrasound imaging beams and ultrasound tracking beams to obtain an interleaved pulse sequence;
synchronize transmission of the interleaved pulse sequence and receipt of the ultrasound tracking beams by a sensor based on establishing a timing pattern for the transmission of the interleaved pulse sequence and the receipt of the ultrasound tracking beams;
transmit the interleaved pulse sequence to the sensor, wherein the sensor receives the ultrasound tracking beams and transmits a response to the ultrasound tracking beams; and
determine, based on the response to the ultrasound tracking beams, a location of the sensor.

10. The non-transitory computer-readable storage medium of claim 9, wherein the instructions, when executed by the processor, further cause the processor to:
generate an image of a region of a patient based on the ultrasound imaging beams;
display the image and the determined location of the sensor in the image.

11. The non-transitory computer-readable storage medium of claim 9, wherein the instructions, when executed by the processor, further cause the processor to:
transmit the ultrasound imaging beams in a region of a patient, and
transmit the ultrasound tracking beams only in a sub-region of the region based on: (i) projecting expected positions of the sensor determined based on historical sensor positions or (ii) processing imaging data from the ultrasound imaging beams.

12. The non-transitory computer-readable storage medium of claim 9, wherein the interleaved pulse sequence comprises a single tracking beam sequence and multiple different imaging beam sequences that vary based on tissue type being imaged.

13. The non-transitory computer-readable storage medium of claim 9, wherein the instructions, when executed by the processor, further cause the processor to:
based on the response to the ultrasound imaging beams received from the sensor, determine signal-to-noise measurements, and
select to enable or disable transmission of the interleaved pulse sequence based on the signal-to-noise measurements.

14. A method for tracking a sensor, the method comprising:
interleaving a pulse sequence of ultrasound imaging beams and ultrasound tracking beams to obtain an interleaved pulse sequence;
synchronizing transmission of the interleaved pulse sequence and receipt of the ultrasound tracking beams by the sensor based on establishing a timing pattern for the transmission of the interleaved pulse sequence and the receipt of the ultrasound tracking beams;
transmitting the interleaved pulse sequence to the sensor, wherein the sensor receives the ultrasound tracking beams and transmits a response to the ultrasound tracking beams;
and determining, based on the response to the ultrasound tracking beams, a location of the sensor.

15. The method of claim 14, further comprising:
based on the response to the ultrasound imaging beams received from the sensor, determining signal-to-noise measurements, and
selecting to enable or disable transmission of the interleaved pulse sequence based on the signal-to-noise measurements.

* * * * *